US00PP27555P3

(12) United States Plant Patent
Mieremet

(10) Patent No.: US PP27,555 P3
(45) Date of Patent: Jan. 17, 2017

(54) ***VERONICA* PLANT NAMED 'FLORVERBLUE'**

(50) Latin Name: *Veronica austriaca*
Varietal Denomination: Florverblue

(71) Applicant: Florensis B.V., Hendrik-Ido-Ambacht (NL)

(72) Inventor: Willem Mieremet, Alphen aan den Rijn (NL)

(73) Assignee: Florensis B.V., Hendrich-Ido-Ambacht (NL)

( * ) Notice: Subject to any disclaimer, the term of this patent is extended or adjusted under 35 U.S.C. 154(b) by 358 days.

(21) Appl. No.: 14/121,141

(22) Filed: Aug. 5, 2014

(65) Prior Publication Data

US 2015/0089700 P1 Mar. 26, 2015

Related U.S. Application Data

(60) Provisional application No. 61/960,542, filed on Sep. 20, 2013.

(51) Int. Cl.
*A01H 5/02* (2006.01)

(52) U.S. Cl.
USPC ..... Plt./251
CPC ..... *A01H 5/02* (2013.01)

(58) Field of Classification Search
USPC ..... Plt./251
CPC ..... A01H 5/02
See application file for complete search history.

(56) References Cited

PUBLICATIONS

GTITM UPOVROM Plant Variety Database Citation for 'Florverblue' as per CA PBR 13/8066; Jun. 26, 2013; 1 page.*

* cited by examiner

*Primary Examiner* — Kent L Bell
(74) *Attorney, Agent, or Firm* — Audrey Charles

(57) ABSTRACT

A new and distinct cultivar of *Veronica* plant named 'Florverblue', characterized by its violet-blue colored flowers, medium green-colored foliage, and moderately vigorous, upright-mounded growth habit, is disclosed.

1 Drawing Sheet

Latin name of genus and species of plant claimed: *Veronica austriaca.*

Variety denomination: 'Florverblue'.

BACKGROUND OF THE INVENTION

The present invention relates to a new and distinct cultivar of *Veronica* plant botanically known as *Veronica austriaca* and hereinafter referred to by the cultivar name 'Florverblue'.

The new cultivar originated in a controlled breeding program in Quedlinburg, Germany, during the summer of 2007. The objective of the breeding program was the development of *Veronica* cultivars with attractive flower coloration and a moderately vigorous, upright-mounded growth habit.

The new *Veronica* cultivar was the result of a self-pollination of *Veronica austriaca* 'Knallblau', not patented, characterized by its medium blue-colored flowers, medium green-colored foliage, and vigorous, upright growth habit. The new cultivar was discovered and selected as a single flowering plant within the progeny of the above stated self-pollination during May 2008 in a controlled environment in Quedlinburg, Germany.

Asexual reproduction of the new cultivar by terminal stem cuttings since May 2008 in Quedlinburg, Germany and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Florverblue' as a new and distinct cultivar of *Veronica* plant:

1. Violet-blue colored flowers;
2. Medium green-colored foliage; and
3. Moderately vigorous, upright-mounded growth habit.

Of the many commercially available *Veronica* cultivars, the most similar in comparison to the new cultivar is the parent 'Knallblau', not patented. However, in side by side comparisons, plants of the new cultivar differ from plants of 'Knallblau' in at least the following characteristics:

1. Plants of the new cultivar have deeper blue-colored flowers than plants of 'Knallblau'; and
2. Plants of the new cultivar are less vigorous and more mounded than plants of 'Knallblau'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Florverblue'. The plants were grown in one-gallon containers for 16 weeks utilizing a soilless growth medium and then transplanted in the field for one week. Plants were pinched two weeks after transplant into the container.

DETAILED BOTANICAL DESCRIPTION

Figure 1:
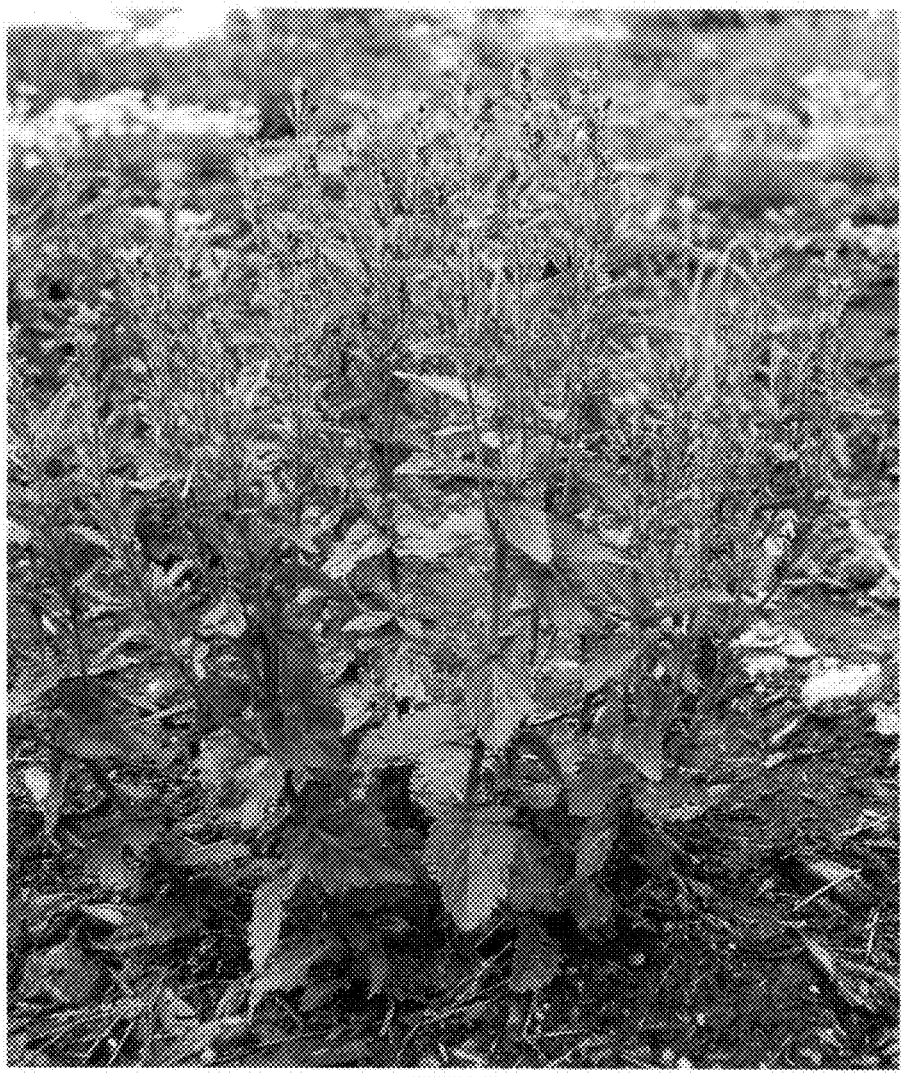
FIG. 1 illustrates a side view of the overall growth and flowering habit of 'Florverblue'.
Figure 2:
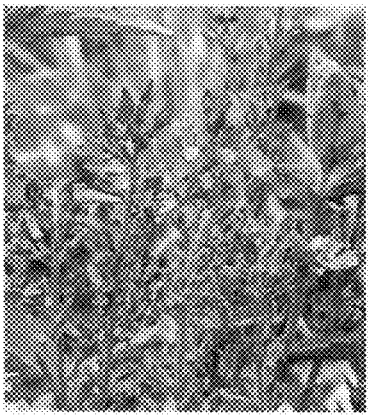
FIG. 2 illustrates a close-up view of the inflorescences of 'Florverblue'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown in a glass-covered greenhouse under conditions comparable to those used in commercial practice. The plants were grown in Elburn, Ill. in one-gallon containers for 16 weeks utilizing a soilless growth medium and then transplanted in the field for one week. Plants were pinched two weeks after transplant into the container. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Veronica austriaca* cultivar Florverblue.

Parentage:

*Female and male parent.*—*Veronica austriaca* 'Knallblau', not patented.

Propagation:

*Type cutting.*—Terminal stem.

*Time to initiate roots.*—Approximately 10 to 12 days.

*Time to produce a rooted cutting.*—Approximately 4 to 5 weeks.

*Root description.*—Fibrous.

*Rooting habit.*—Freely branching.

Plant description:

*Commercial crop time.*—Approximately 16 to 18 weeks from a rooted cutting to finish in a 15 cm pot. During this period, at least 5 weeks below 45° F. during the night is required to initiate flowering.

*Growth habit and general appearance.*—Moderately vigorous, upright-mounded.

*Size.*—Height from soil level to top of plant plane: Approximately 26.0 cm. Width: Approximately 30.0 cm.

*Branching habit.*—Freely branching, pinching enhances basal branching. Quantity of main branches per plant: Approximately 6.

*Branch.*—Strength: Moderate. Branch height to bottom on inflorescence: Approximately 15.0 cm. Diameter: Approximately 3.0 mm. Length of central internode: Approximately 2.5 cm. Texture: Densely pubescent with appressed and curled hairs. Color of young and mature stem: 147C.

Foliage description:

*General description.*—Quantity of leaves per main branch: Approximately 12. Fragrance: None detected. Form: Simple. Arrangement on flowering stem: Opposite.

*Leaves.*—Aspect: Perpendicular to stem. Shape: Ovate. Margin: Serrate. Apex: Broadly accute. Base: Rounded, sessile. Venation pattern: Pinnate. Length of mature leaf: Approximately 3.0 cm. Width of mature leaf: Approximately 2.2 cm. Texture of upper surface: Sparsely pubescent with appressed hairs. Texture of lower surface: Densely pubescent with appressed and curled hairs. Color of upper surface of young and mature foliage: 137A. Color of lower surface of young and mature foliage: Closest to 137B. Venation of upper and lower surface: 147C.

Flowering description:

*Flowering habit.*—'Florverblue' flowers during early spring to late spring under outdoor conditions.

*Lastingness of individual flower on the plant.*—Approximately 7 days.

Inflorescence description:

*General description.*—Type: Terminal raceme, self-cleaning. Fragrance: Faint. Height: Approximately 10.0 cm. Width: Approximately 4.0 cm. Quantity per plant: Approximately 7.

*Peduncle.*—Strength: Strong. Aspect: Erect. Length: Approximately 3.5 cm. Diameter: Approximately 2.0 mm. Texture: Densely pubescent with appressed and curled hairs. Color: 147B.

Flower description:

*General description.*—Type: Single, campanulate. Aspect: Outward. Quantity per inflorescence: Approximately 9.

*Bud.*—Rate of opening: Generally takes 3 to 4 days for bud to progress from first color to fully open flower. Quantity per inflorescence: Approximately 7.

*Bud just before opening.*—Shape: Oblong. Length: Approximately 4.0 mm. Diameter: Approximately 2.0 mm. Texture: Glabrous. Color: 94A.

*Corolla.*—Height: Approximately 7.0 mm. Diameter: Approximately 1.3 cm.

*Petals.*—Quantity: 4, in a single whorl. Appearance: Dull. Shape: Elliptic. Margin: Entire. Apex: Broadly acute. Base: Cuneate, lower 1.0 mm fused. Length: Approximately 5.0 mm to 6.0 mm on a single flower. Width: Approximately 4.0 mm to 6.0 mm on a single flower. Texture of upper and lower surfaces: Glabrous. Color of upper surface when first open: 94A with NN155D at tube opening. Color of lower surface when first and fully open: 94B with NN155D at base. Color of upper surface when fully open: Between 94A and 94B with venation of 94A and NN155D at tube opening. Tube length: Approximately 1.0 mm. Tube opening: Approximately 1.0 mm. Color of whiskers surrounding tube opening: NN155D.

*Caylx.*—Diameter: Approximately 3.0 mm.

*Sepals.*—Quantity per flower: 4. Shape: Lanceolate, fused at base. Apex: Acute. Length: Two larger sepals approximately 4.0 mm and two smaller sepals approximately 2.0 mm. Width: Two larger sepals approximately 2.0 mm and two smaller sepals approximately 1.0 mm. Texture of upper surface: Glabrous. Texture of lower surface: Moderately pubescent with appressed hairs. Color of upper and lower surfaces: 137A.

*Pedicel*.—Strength: Strong, flexible. Aspect: Approximately 45° angle from vertical. Length: Approximately 2.0 mm. Diameter: Approximately 0.5 mm. Texture: Densely pubescent with appressed and curled hairs. Color: 147B.

*Reproductive organs*.—Androecium: Stamen quantity: 2 per flower. Stamen length: Approximately 6.0 mm. Filament color: NN155D with an overlay of 94B on upper half. Anther shape: Sagittate, dorsifixed. Anther length: Approximately 1.0 mm. Anther color: 93B. Pollen amount: Sparse. Pollen color: 155D. Gynoecium: Pistil quantity: 1 per flower. Pistil length: Approximately 6.0 mm. Stigma shape: Clavate. Stigma length: Less than 1.0 mm. Stigma color: 160B. Style length: Approximately 6.0 mm. Style color: 93B. Ovary diameter: Approximately 1.0 mm. Ovary color: 144A.

Seed and fruit production: Neither seed nor fruit production has been observed.

Disease and pest resistance: Resistance to pathogens and pests common to *Veronica* has not been observed.

What is claimed is:

1. A new and distinct cultivar of *Veronica* plant named 'Florverblue', substantially as herein illustrated and described.

* * * * *